United States Patent
Inoue et al.

(10) Patent No.: US 12,029,630 B2
(45) Date of Patent: Jul. 9, 2024

(54) APPARATUS AND METHOD FOR MANUFACTURING ABSORBENT ARTICLE

(71) Applicant: ZUIKO CORPORATION, Osaka (JP)

(72) Inventors: Daisuke Inoue, Osaka (JP); Takashi Arima, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 385 days.

(21) Appl. No.: 17/413,683

(22) PCT Filed: Nov. 12, 2019

(86) PCT No.: PCT/JP2019/044318
§ 371 (c)(1),
(2) Date: Jun. 14, 2021

(87) PCT Pub. No.: WO2020/137206
PCT Pub. Date: Jul. 2, 2020

(65) Prior Publication Data
US 2022/0008256 A1    Jan. 13, 2022

(30) Foreign Application Priority Data
Dec. 28, 2018 (JP) ................................. 2018-247299

(51) Int. Cl.
*A61F 13/15* (2006.01)

(52) U.S. Cl.
CPC .............................. *A61F 13/15764* (2013.01)

(58) Field of Classification Search
CPC ..................... A61F 13/15764; A61F 13/15674
See application file for complete search history.

(56) References Cited

U.S. PATENT DOCUMENTS

| | | | |
|---|---|---|---|
| 7,347,914 B2 * | 3/2008 | Umebayashi | ..... A61F 13/15593 156/290 |
| 7,438,779 B2 * | 10/2008 | Nakakado | ......... A61F 13/15593 156/259 |
| 2005/0241751 A1 * | 11/2005 | Nakakado | .............. B26D 1/405 156/229 |

(Continued)

FOREIGN PATENT DOCUMENTS

| | | | | |
|---|---|---|---|---|
| EP | 2612632 A1 * | 7/2013 | ....... | A61F 13/15577 |
| EP | 3 395 309 A1 | 10/2018 | | |

(Continued)

OTHER PUBLICATIONS

International Search Report for corresponding Application No. PCT/JP2019/044318, mailed Feb. 4, 2020.

*Primary Examiner* — Gene O Crawford
*Assistant Examiner* — Abby A Jorgensen
(74) *Attorney, Agent, or Firm* — Renner, Otto, Boisselle & Sklar, LLP (57) ABSTRACT

The present apparatus for manufacturing an article includes a velocity-changing device that changes velocity so that circumferential velocity of a holding pad is continuously decelerated or continuously accelerated during a period from a first start time, at which hand-over of a workpiece of a first size at an upstream position as a hand-over position on a circling path is started, to a second start time, at which hand-over of a workpiece of a second size at a downstream position as the hand-over position downstream of the upstream position on the circling path is started.

19 Claims, 5 Drawing Sheets

(56) References Cited

U.S. PATENT DOCUMENTS

| | | |
|---|---|---|
| 2015/0223992 A1 | 4/2015 | Maehara |
| 2015/0272786 A1* | 10/2015 | Piantoni ............ A61F 13/15674 493/347 |
| 2016/0250080 A1* | 9/2016 | Wada ..................... B65G 47/64 198/364 |

FOREIGN PATENT DOCUMENTS

| | | | | |
|---|---|---|---|---|
| JP | 2002253606 A | * | 9/2002 | |
| JP | 2010-142414 A | | 7/2010 | |
| JP | 2013255624 A | * | 12/2013 | |
| WO | WO-2005085108 A1 | * | 9/2005 | ............. B65H 20/04 |
| WO | WO-2014060923 A1 | * | 4/2014 | ....... A61F 13/15674 |
| WO | WO-2016170947 A1 | * | 10/2016 | |

* cited by examiner

APPARATUS AND METHOD FOR MANUFACTURING ABSORBENT ARTICLE

TECHNICAL FIELD

The present invention relates to an apparatus and method for manufacturing absorbent articles, and particularly to conveying workpieces.

BACKGROUND ART

With conventional methods, when conveying a workpiece of an absorbent article, the holding pad picks up the workpiece at the pick-up position, thereafter accelerates or decelerates, and then hands over the workpiece onto the sheet at the hand-over position. With the apparatus disclosed in the first patent document identified below, a plurality of hand-over positions are provided, and the velocity of the holding pad is varied depending on the size of the article to be manufactured.

CITATION LIST

Patent Document

[FIRST PATENT DOCUMENT] JP2010-142414 A (FIG. 5)

SUMMARY OF INVENTION

Typically, a velocity-changing cam mechanism is employed to accelerate/decelerate the velocity of the holding pad. However, with the invention of the first patent document, the holding pad is at a constant velocity at the two hand-over positions. Thus, there are a plurality of constant-velocity regions, which is a factor for imposing a large load on the cam mechanism.

Figure 5:
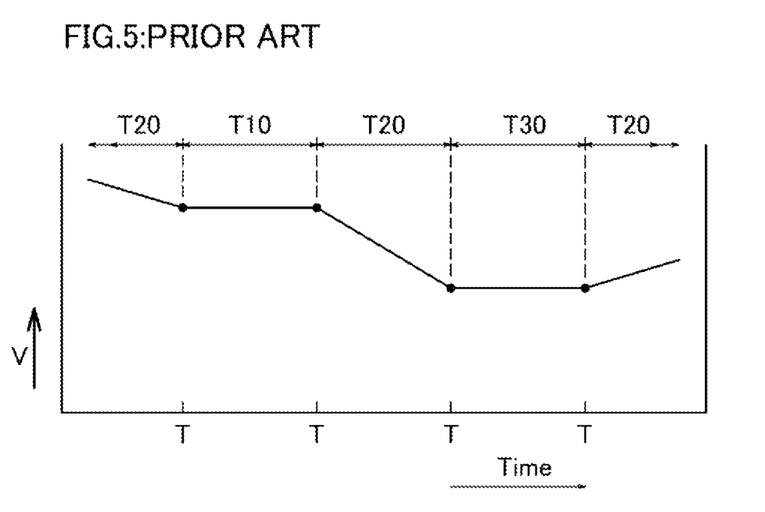
FIG. 5 is a velocity diagram showing the change in the velocity of the pad of a conventional apparatus.

Such an issue will be described in detail with reference to FIG. 5, which shows a conventional velocity diagram.

Where workpieces are handed over onto the sheet at a plurality of positions, i.e., the upstream position and the downstream position, there are two constant-velocity periods T10 and T30 where the velocity of the holding pad is constant, as shown in FIG. 5. There are accelerating/decelerating periods T20 where the pad is accelerated/decelerated before and after the two constant-velocity periods T10 and T30.

When such constant velocity and acceleration/deceleration are repeated, the cam mechanism is subjected to a load every cycle at points in time T, at which acceleration changes. This load lowers the durability of the cam mechanism, necessitating early maintenance.

While the velocity of the holding pad may be accelerated/decelerated by controlling the rotation speed of the servomotor, the load on the servomotor increase also in this case due to the plurality of constant-velocity regions.

Thus, it is an object of the present invention to provide an apparatus and method for manufacturing an absorbent article that can accommodate changes in the size of the article to be manufactured without imposing a large load on the equipment.

An apparatus of the present invention includes:

a holding pad that rotates along a circling path while velocity thereof is changed to pick up a workpiece at a pick-up position and hand over the workpiece onto a continuous sheet at a hand-over position;

a conveying device that conveys the continuous sheet at conveying velocity that depends on a size of a product to receive and convey the workpiece on the continuous sheet at the hand-over position; and a velocity-changing device that changes velocity so that circumferential velocity V of the holding pad is continuously decelerated or continuously accelerated during a period from a first start time S1, at which hand-over of the workpiece for a first-size product at an upstream position as the hand-over position on the circling path is started, to a second start time S2, at which hand-over of the workpiece for a second-size product at the downstream position as the hand-over position downstream of the upstream position on the circling path is started.

A method of the present invention includes:

a first conveying step of using a holding pad that rotates along a circling path while velocity thereof is changed to pick up a workpiece at a pick-up position and hand over the workpiece onto a continuous sheet at a hand-over position;

a second conveying step of using a conveying device to convey the continuous sheet at conveying velocity $V_N$ that depends on a size of a product to receive and convey the workpiece on the continuous sheet at the hand-over position;

a step of setting in advance the hand-over position to be one position selected between an upstream position and a downstream position on the circling path, the downstream position being downstream of the upstream position, depending on the size; and a velocity-changing step in which a velocity-changing device changes velocity so that circumferential velocity V of the holding pad is continuously decelerated or continuously accelerated during a period from a first start time S1, at which hand-over of the workpiece for a first-size product at the upstream position is started, to a second start time S2, at which hand-over of the workpiece for a second-size product at the downstream position is started.

According to the present invention, it is possible to select the upstream position and the downstream position so as to hand over the workpiece of the first or second size onto the conveying device at the respective positions. Therefore, it is possible to manufacture, with a single apparatus, articles of different sizes.

Particularly, during a period from the first start time S1 to the second start time S2, the velocity does not become a constant velocity but is continuously decelerated or accelerated. Therefore, it is possible to reduce the load on parts such as the cams and the servomotor.

Note that when manufacturing three or more sizes with a single apparatus, a position may be set for handing over a workpiece of the third size.

DESCRIPTION OF EMBODIMENTS

Preferably, the velocity-changing device 2 changes velocity so that the circumferential velocity V is continuously decelerated during a period from the first start time S1 to the second start time S2.

According to the present invention, the continuous sheet is conveyed at a generally constant velocity that depends on the size, whereas the pad circles at a non-constant velocity when handing over the workpiece. Therefore, when the workpiece is placed on the sheet while the pad is accelerating, the workpiece may likely be creased.

In contrast, when the workpiece is placed on the sheet while the pad is decelerating, the workpiece is likely to be stretched in the conveying direction and unlikely to be creased. Therefore, by handing over the workpiece while decelerating, the workpiece is likely to be neatly placed on the sheet, thereby facilitating bonding between the sheet and the workpiece.

Preferably, for the first size, the conveying velocity is set to the circumferential velocity V of the holding pad at the first start time S1; and for the second size, the conveying velocity is set to the circumferential velocity V of the holding pad at the second start time S2.

In this case, when handing over the workpiece W onto the continuous sheet N, the workpiece W is unlikely to be creased.

Preferably, the velocity-changing device changes the velocity of the holding pad so that the circumferential velocity V is continuously decelerated or continuously accelerated over a first period T1 from the first start time S1 to a first completion time C1, at which hand-over of the workpiece of the first size is completed, a second period T2 from the first completion time C1 to the second start time S2, and a third period T3 from the second start time S2 to a second completion time C2, at which hand-over of the workpiece of the second size at the downstream position is completed.

In this case, the velocity is continuously decelerated or accelerated not only in the first and second periods T1 and T2 but also in the third period T3. Therefore, it is possible to further reduce the load on the parts.

Preferably, the apparatus further includes a setting device for setting the upstream position P1 or the downstream position P2 as the hand-over position.

More preferably, the conveying device includes a transfer roll that contacts the holding pad with the continuous sheet and the workpiece therebetween; and the setting device positions the transfer roll at one of the upstream position and the downstream position.

While the transfer roll may be provided at each of the upstream position and the downstream position, the transfer roll at the upstream position and the transfer roll at the downstream position are then arranged spaced apart from each other so as to avoid interference between the transfer rolls, and the degree of freedom in selecting the position is likely to be low.

In contrast, allowing the transfer roll to be moved between the upstream position and the downstream position and selectively fixed to the frame increases the degree of freedom in selecting the position. This increases the degree of freedom in selecting the circumferential velocity V at the time of hand-over at each position.

When the deceleration ratio is too large, the stretch of the workpiece will be excessive, whereas when the deceleration ratio is 1.0, i.e., constant velocity, the advantageous effects of the present invention will not be realized.

From such a viewpoint, when decelerating, preferably, a deceleration ratio of the circumferential velocity V at the second start time S2 relative to the circumferential velocity V at the first start time S1 is set to be greater than 1.0 and 1.2 or less, preferably 1.07 or less, and more preferably 1.01 or less.

When the acceleration ratio is too large, the workpiece will be creased, whereas when the acceleration ratio is 1.0, i.e., constant velocity, the advantageous effects of the present invention will not be realized.

From such a viewpoint, when accelerating, preferably, an acceleration ratio of the circumferential velocity V at the second start time S2 relative to the circumferential velocity V at the first start time S1 is greater than 1.0 and 1.2 or less, preferably 1.07 or less, and more preferably 1.01 or less.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

EMBODIMENTS

Embodiments of the present invention will now be described with reference to the drawings.

First, prior to describing the present embodiment, an example of a worn article (absorbent article), which is an application thereof, will be described.

Figure 4:
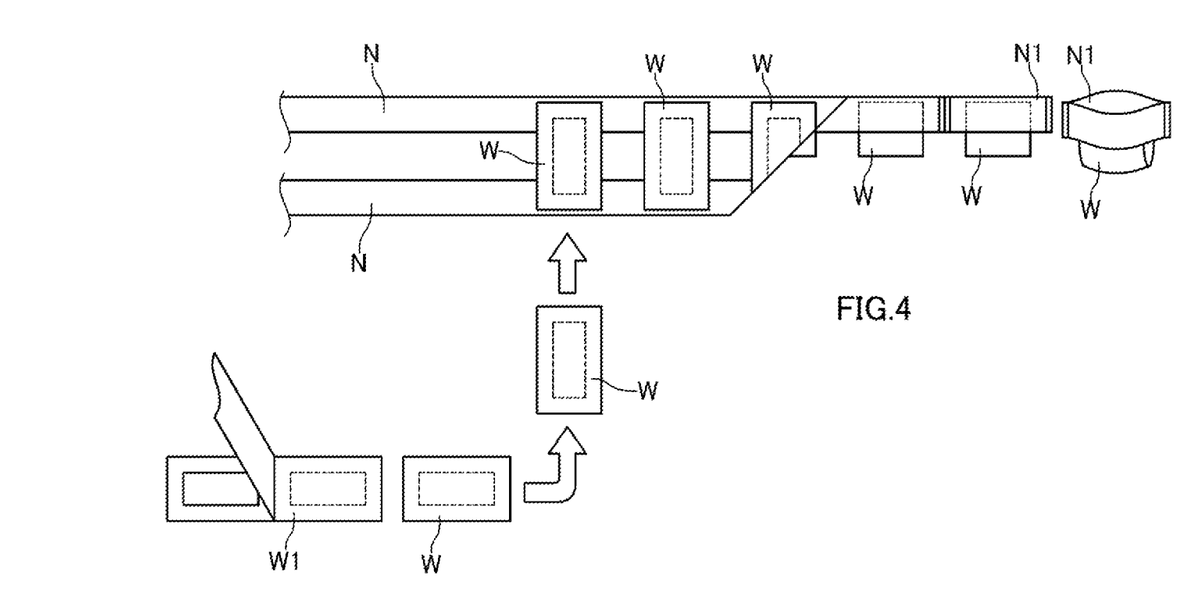
FIG. 4 is a schematic process diagram showing an example of a worn article and a manufacturing method thereof.

FIG. 4 schematically shows a method for manufacturing a worn article.

In this figure, worn articles are produced from a continuous sheet N and workpieces (absorbent bodies) W. The continuous sheet N is a nonwoven fabric with elastic members arranged along its longitudinal direction, for example, and there may be a pair of continuous sheets N.

Workpieces W are cut into units of articles from the continuous laminate W1, and then separated from the continuous laminate W1, after which they are turned 90° to be provided so as to bridge between a pair of continuous sheets N and N. The workpieces W provided so as to bridge between the continuous sheets are folded in two and then cut into units of worn articles N1.

Next, the outline of a present manufacturing apparatus will be described.

Figure 1:
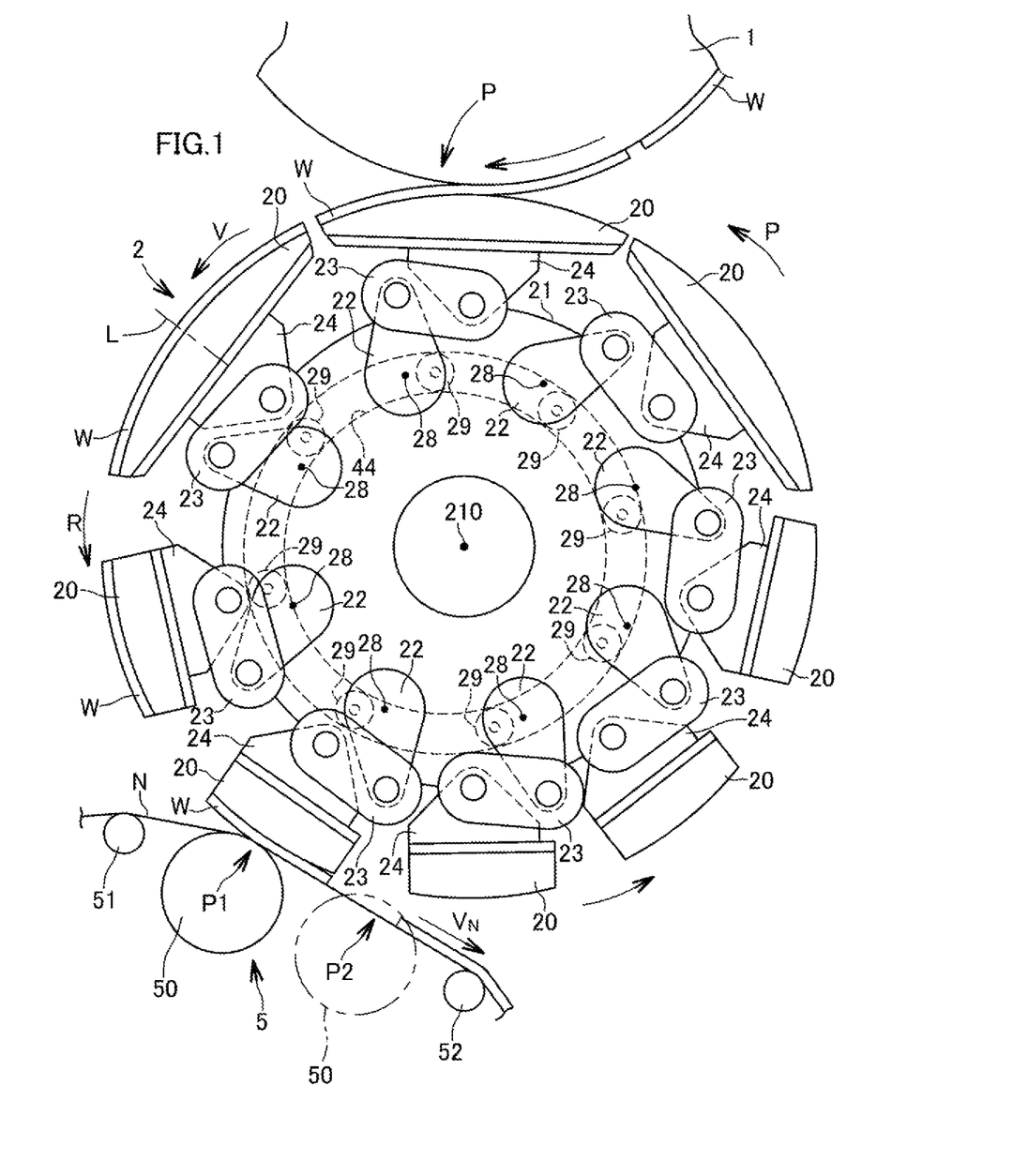
FIG. 1 is a schematic layout diagram showing an embodiment of an apparatus for conveying a workpiece of the present invention.

In FIG. 1, the present manufacturing apparatus includes an upstream hand-over roll 1, a velocity-changing device 2 and a conveying device 5. The velocity-changing device 2 includes a plurality of holding pads 20. The hand-over roll 1 and the holding pads 20 convey workpieces W. The conveying device 5 conveys the continuous sheet N and the workpieces W on the continuous sheet N.

The holding pad 20 circles, while changing its velocity, along the circling path of the velocity-changing device 2, picks up the workpiece W from the hand-over roll 1 at the pick-up position P, and hands over the workpiece W onto the continuous sheet N at the hand-over position P1, P2. The hand-over positions include the upstream position P1 and the downstream position P2. The upstream position P1 or the downstream position P2 is the hand-over position for when the size of the worn article is the first size or the second size, respectively.

The conveying device 5 conveys the continuous sheet N at conveying velocity $V_N$ that depends on the size of the product to receive and convey the workpiece W on the continuous sheet N at the hand-over position P1 or P2. For example, the conveying velocity $V_N$ may be a high velocity $V1_S$ for the first size (size L), and may be a lower velocity $V2_S$ for the second size (size M). The conveying device 5 in this embodiment includes a transfer roll 50 and guide rolls 51 and 52 arranged upstream and downstream of the transfer roll 50, and conveys the continuous sheet N continuously from the upstream side to the downstream side.

Figure 3A:
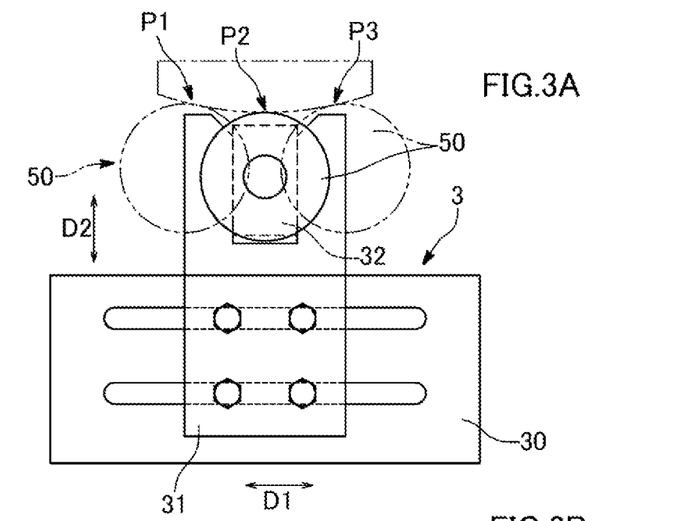
FIG. 3A is a schematic front view showing an example of a setting device.

The conveying device 5 includes a setting device 3 as shown in FIG. 3A, for example. The setting device 3 is for setting the hand-over position to either the upstream position P1 or the downstream position P2. The transfer roll 50 of FIG. 1 contacts the holding pad 20 with the continuous sheet N and the workpiece W therebetween. The setting device 3 positions the transfer roll 50 at one of the upstream position P1 and the downstream position P2.

Next, an example of the structure of the setting device 3 will be described using FIG. 3A.

In FIG. 3A, the setting device 3 includes a fixed frame 30, a first movable frame 31 and a second movable frame 32. The first movable frame 31 is attached to the fixed frame 30 so as to be movable, relative to the fixed frame 30, in the tangential direction D1 of the circling direction R of the holding pad 20.

On the other hand, the second movable frame 32 is attached to the first movable frame 31 so as to be movable, relative to the first movable frame 31, in the normal direction D2 of the circling direction R of the holding pad 20. The second movable frame 32 axially supports the transfer roll 50, and the transfer roll 50 can therefore be freely fixed at the upstream position P1 or the downstream position P2 or any other position.

Next, the velocity-changing device 2 of this embodiment will be described in detail.

As shown in FIG. 1, a plurality of crank arms 22 are arranged on a driven wheel 21 at regular angular intervals therebetween. The intervals between the crank arms 22 are invariable, and arm centers 28, which are the centers of rotation of these crank arms 22, rotate at the same angular velocity together with the driven wheel 21.

A velocity-changing cam roller 29 is provided at a position spaced apart from the arm center 28 of each crank arm 22. The cam rollers 29 move along a velocity-changing cam groove 44. The velocity-changing cam groove 44 is invariable and eccentric with a center of drive 210, which is the center of rotation of the driven wheel 21. Therefore, the distance from the center of drive 210 to the cam roller 29 periodically expands and contracts depending on the position of the cam roller 29 and the cam groove 44.

Therefore, the crank arm 22 swings periodically within a certain angular range, and the tip of the crank arm 22 swings periodically. That is, the tip of the crank arms 22 is displaced in the conveying direction along the circling direction R relative to the arm center 28 of the crank arm 22 on the left side shown in FIG. 1, and is displaced in the reverse direction on the right side shown in FIG. 1.

A link lever 23 that is pin-linked to the tip of the crank arm 22 and a link block 24 that is pin-linked to the link lever 23 are displaced in conjunction with the swing of the tip of the crank arm 22. As the crank arm 22 swings, the distance between the arm center 28 of the crank arm 22 and the link block 24 changes, thereby also changing the interval between adjacent link blocks 24. As a result, this changes the angular velocity of the holding pad 20 linked to the link block 24 and the interval between the holding pads 20 and 20 in the circling direction R.

As shown in FIG. 1, in this embodiment, the holding pad 20 turns, relative to the link block 24, 90° about the normal direction L to the circling direction R, thereby turning the workpiece W 90° as shown in FIG. 4. That is, the holding pad 20 of FIG. 1 picks up the workpiece W at the pick-up position P, turns while changing the velocity to circle to the hand-over position P1 (P2), and hands over the workpiece W onto the continuous sheet N at the hand-over position.

After the hand-over action, the holding pad 20 turns while changing the velocity while the holding pad 20 circles in the circling direction R from the hand-over position P1 (P2), and the holding pad 20 circles to the pick-up position P, and picks up the workpiece W at the pick-up position P. Each holding pad 20 continuously performs these actions, thereby successively placing workpieces W of FIG. 4 onto the pair of continuous sheets N.

Note that the mechanism by which the holding pad 20 of FIG. 1 turns 90° about the normal direction L may include a peripheral cam, or the like, well known in the art. For example, such a mechanism is described in WO2005/075163, the entire disclosure of which is herein incorporated by reference.

The holding pad 20 sucks the workpiece W by negative pressure at the pick-up position P and then holds the workpiece W, and the holding pad 20 circles along the circling direction R and releases the negative pressure upstream of the hand-over position P1 (P2). On the other hand, the conveying device 5 activates negative pressure at the hand-over position P1, P2 to receive the workpiece W on the continuous sheet N.

When the upstream position P1 and the downstream position P2 are close to each other as in this embodiment, the area over which negative pressure is applied to the holding pad 20 may be constant. However, when the upstream position P1 and the downstream position P2 are distant from each other (JP2010-142414 A), the area may need to be varied.

Next, the velocity-changing device 2 and the velocity-changing step of FIG. 1 will be described in detail.

The hand-over position is set in advance to be one position selected between the upstream position P1 and the downstream position P2 on the circling path, the downstream position P2 being downstream of the upstream position P1, depending on the size. That is, for the first size (size L), the transfer roll 50 is fixed at the upstream position P1. On the other hand, for the second size (size M), the transfer roll 50 is fixed at the downstream position P2.

Figure 2:
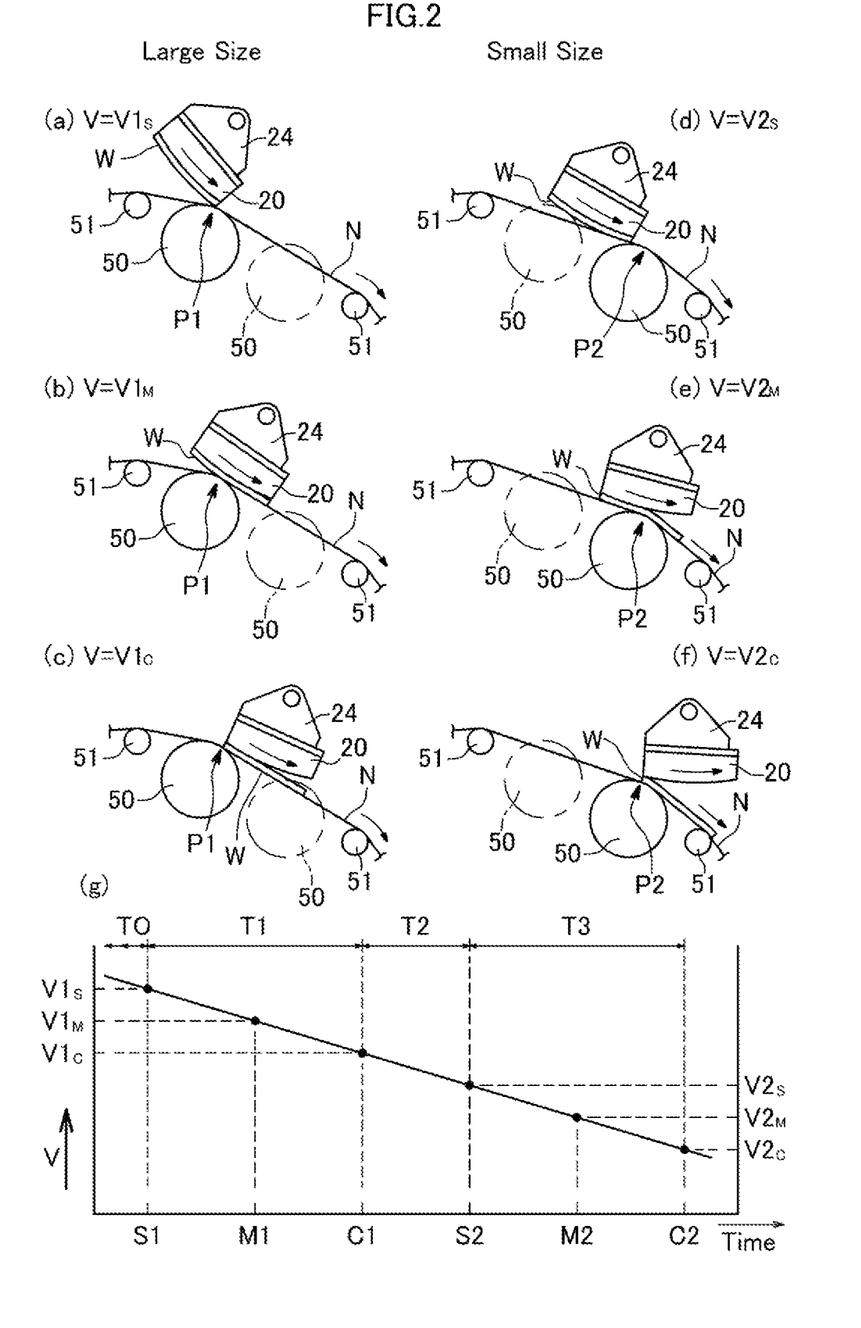
FIGS. 2(a) to 2(f) are front views showing the operation of the pad.
FIG. 2(g) is a velocity diagram showing the change in the velocity of the pad.

FIGS. 2(*a*) to 2(*c*) show the hand-over step for the first size, and FIGS. 2(*d*) to 2(*f*) show the hand-over step for the second size. FIG. 2(*g*) is a velocity diagram showing the change in the velocity of the holding pad 20.

In FIG. 2(*g*), different points in time are defined as follows.

First start time S1: a point in time when the hand-over of the workpiece W for the first size at the upstream position P1 of FIG. 2(*a*) is started.

First completion time C1: a point in time when the hand-over of the workpiece W for the first size at the upstream position P1 of FIG. 2(c) is completed.

First middle time M1: a point in time that is in the middle between the first start time S1 and the first completion time C1 (see FIG. 2(b)).

Second start time S2: a point in time when the hand-over of the workpiece W for the second size at the downstream position P2 of FIG. 2(d) is started.

Second completion time C2: a point in time when the hand-over of the workpiece W for the second size at the downstream position P2 of FIG. 2(f) is completed.

Second middle time M2: a point in time that is in the middle between the second start time S2 and the second completion time C2 (see FIG. 2(e)).

In this embodiment, different periods T0 to T3 of FIG. 2(g) are defined as follows.

T0: a pre-start period before the first start time S1 of FIG. 2(g).

T1: a first period from the first start time S1 to the first completion time C1.

T2: a second period from the first completion time C1 to the second start time S2.

T3: a third period from the second start time S2 to the second completion time C2.

In this embodiment, the velocity-changing device 2 changes the velocity of the holding pad 20 so that the circumferential velocity V of the holding pad 20 is continuously decelerated over the pre-start period T0, the first period T1, the second period T2 and the third period T3.

This deceleration (velocity changing) step will be described in detail.

For the first size, the transfer roll 50 of FIG. 1 is fixed at the upstream position P1 represented by a solid line, and the circumferential velocity V is continuously decelerated to be $V1_S$, $V1_M$ and $V1_C$ at points in time S1, M1 and C1 of FIG. 2(g), respectively.

For the first size, the holding pad 20 is similarly continuously decelerated also in the pre-start period T0, which is prior to the first period T1, the second period T2 and the third period T3.

For the second size, the transfer roll 50 of FIG. 1 is fixed at the downstream position P2 represented by a two-dot-chain line, and the circumferential velocity V is continuously decelerated to be $V2_S$, $V2_M$ and $V2_C$ at points in time S2, M2 and C2 of FIG. 2(g).

For the second size, the holding pad 20 is similarly continuously decelerated also in the pre-start period T0, which is prior to the third period T3, the first period T1 and the second period T2.

Therefore, the holding pad 20 of FIG. 2 is continuously decelerated at and before and after the hand-over position P1 (P2), i.e., over the periods T0 to T3. Therefore, there is little load on the cam groove 44 and the cam rollers 29 of FIG. 1, irrespective of the size.

On the other hand, for the first size and the second size, the conveying velocity $V_N$ of the continuous sheet N by the conveying device 5 may be set to respective constant velocities of $V1_S$ and $V2_S$.

That is, for the first size, the conveying velocity $V_N$ may be set to the circumferential velocity V of the holding pad 20 at the first start time S1, at which the hand-over of the workpiece W of the first size is started, i.e., $V1_S$. In this case, during the hand-over step of FIGS. 2(a) to 2(c), the workpiece W is subjected to a pulling force in the conveying direction of the continuous sheet N. Therefore, the workpiece W is unlikely to be creased.

Similarly, for the second size, the conveying velocity $V_N$ may be set to the circumferential velocity V of the holding pad 20 at the second start time S2, at which the hand-over of the workpiece W of the second size is started, i.e., $V2_S$. In this case, during the hand-over step of FIGS. 2(d) to 2(f), the workpiece W is subjected to a pulling force in the conveying direction of the continuous sheet N. Therefore, the workpiece W is unlikely to be creased.

While the circumferential velocity V is continuously decelerated over the periods T0 to T3 as shown in FIG. 2(g) in this embodiment, the circumferential velocity V may be continuously accelerated. In this case, the conveying velocity $V_N$ may be set to the circumferential velocity V of the holding pad 20 at the first completion time C1 for the first size (size M), and the conveying velocity $V_N$ may be set to the circumferential velocity V of the holding pad 20 at the second completion time C2 for the second size (size L).

As shown in FIG. 2(g), in this embodiment, the deceleration ratio of the circumferential velocity V is set to be constant over the periods T0 to T3. However, the deceleration ratios (degrees of deceleration) of the periods T0 to T3 may be different from each other.

While this embodiment is directed to a case where worn articles of two sizes are manufactured, there may be three or more sizes.

When manufacturing worn articles of the first to third sizes, the transfer roll 50 may receive the workpiece W at the upstream position P1, the downstream position P2 and the most downstream position P3 as indicated by solid and two-dot-chain lines of FIG. 3A.

Figure 3B:
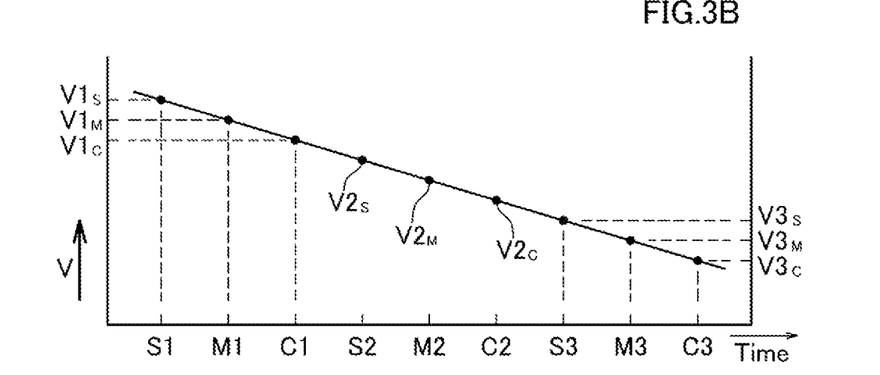
FIG. 3B is another example of a velocity diagram of the pad.

When the hand-over is done at the positions P1 to P3 for the first to third sizes, the velocity of the circumferential velocity V of the holding pad 20 may be decelerated as shown in FIG. 3B. Note that in this case, the circumferential velocity V of the holding pad 20 may be set to even smaller velocities, such as $V3_S$, $V3_M$ and $V3_C$, at the third start time S3, the third middle time M3 and the third completion time C3, respectively, for the workpiece W of the third size (size S).

As described above, the holding pad 20 of FIG. 1 is repeatedly accelerated and decelerated for each rotation. Therefore, when transitioning from deceleration to acceleration and when transitioning from acceleration to deceleration, there are periods of a generally constant velocity. Such constant velocity periods may occur in the hand-over step.

Figure 3C:
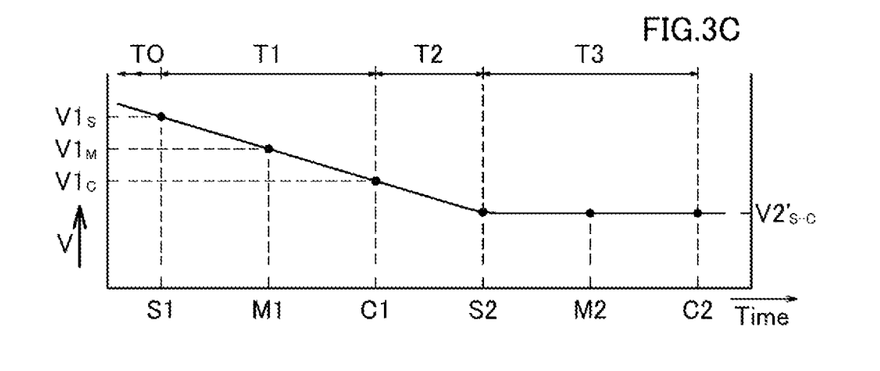
FIG. 3C is still another example of a velocity diagram of the pad.

For example, as shown in the velocity diagram of FIG. 3C, the velocity may be a generally constant velocity V2's-c during the third period T3, i.e., from the second start time S2 to the second completion time C2. In other words, the velocity-changing device 2 may change the velocity so that the circumferential velocity V of the holding pad 20 of FIG. 1 is continuously decelerated during a period from the first start time S1, at which the hand-over of the workpiece W of the first size at the upstream position P1 (FIG. 1) is started, to the second start time S2, at which the hand-over of the workpiece W of the second size at the downstream position P2 (FIG. 1) is started.

Now, the point in time when the negative pressure acts on the holding pad 20 may be changed in response to the change of the size. Note that when the positions P1 to P3 are as close to each other as shown in FIG. 1 to FIG. 3A, there may be cases where there is no need to change the period in which the negative pressure acts.

Transfer rolls may be individually provided at the respective hand-over positions P1 and P2.

When two transfer rolls 50 of FIG. 1 are individually provided at the upstream position P1 and the downstream position P2, the setting device is implemented as a structure for fixing the transfer rolls 50 and 50. Even when two transfer rolls 50 and 50 are individually provided, it will be necessary to employ a structure such that the transfer rolls 50 of FIG. 3A can be slightly advanced/retracted in the normal direction D2.

Note that the transfer roll 50 of FIG. 1 may be fixed at one position, and a setting device (not shown) may be used to set the upstream position P1 and the downstream position P2 by slightly rotating the velocity-changing device 2 as a whole.

While preferred embodiments have been described above with reference to the drawings, obvious variations and modifications will readily occur to those skilled in the art upon reading the present specification.

For example, the workpiece does not need to be rotated 90 degrees about the normal direction while the workpiece moves from the pick-up position to the hand-over position. The length in the circumferential direction of the holding pad at the hand-over position may be shorter than that at the pick-up position, or they may be equal to each other.

The velocity of the holding pad at the pick-up position may be a constant velocity from the start of the pick-up until the completion of the pick-up.

Thus, such variations and modifications shall fall within the scope of the present invention as defined by the appended claims.

INDUSTRIAL APPLICABILITY

The present invention is applicable to conveying during the manufacture of various absorbent articles such as disposable pants and diapers.

REFERENCE SIGNS LIST

1: Hand-over roll
2: Velocity-changing device, 20: Holding pad
21: Driven wheel, 210: Center of drive, 22: Crank arm, 28: Arm center
29: Cam roller, 23: Link lever, 24: Link block
3: Setting device, 30: Fixed frame, 31, 32: Movable frame
44: Cam groove
5: Conveying device, 50: Transfer roll
S1 (S2): First (second) start time
C1 (C2): First (second) completion time
P: Pick-up position, P1: Upstream position, P2: Downstream position, P3: Most downstream position
R: Circling direction
T1 to T3: First to third periods
L: Normal line
V: Circumferential velocity, $V_N$: Conveying velocity
N: Continuous sheet, W: Workpiece

The invention claimed is:

1. An apparatus for manufacturing an absorbent article, the apparatus comprising:
    a holding pad that rotates along a circling path while velocity of the holding pad is changed to pick up a workpiece at a pick-up position and hand over the workpiece onto a continuous sheet at a hand-over position;
    a conveying device that conveys the continuous sheet at conveying velocity that depends on a size of a product to receive and convey the workpiece on the continuous sheet at the hand-over position, wherein the conveying device includes a transfer roll contacting with the holding pad via the continuous sheet and the workpiece; and
    a velocity-changing device that changes circumferential velocity of the holding pad during a period from a first start time to a second start time,
    when the size of the product is a first size, hand-over of the workpiece starts at the first start time at an upstream position, which is the hand-over position on the circling path,
    when the size of the product is a second size, hand-over of the workpiece starts at the second start time at a downstream position, which is the hand-over position downstream of the upstream position on the circling path, and
    the velocity-changing device changing the circumferential velocity of the holding pad so that the circumferential velocity is continuously decelerated or continuously accelerated during the period from the first start time to the second start time,
    a setting device comprising a moveable frame configured to change a physical position of the transfer roll, such that the physical position of the transfer roll is changeable between the upstream position and the downstream position, and
    wherein the moveable frame changing the physical position of the transfer roll results in a change in the hand-over position accordingly between the upstream position and the downstream position.

2. The apparatus for manufacturing an absorbent article according to claim 1, wherein the velocity-changing device changes velocity so that the circumferential velocity is continuously decelerated during the period from the first start time to the second start time.

3. The apparatus for manufacturing an absorbent article according to claim 1, wherein the velocity-changing device changes the velocity of the holding pad so that the circumferential velocity is continuously decelerated or continuously accelerated over a first period, a second period, and a third period,
    the first period being from the first start time to a first completion time, at which hand-over of the workpiece of the first size is completed,
    the second period being from the first completion time to the second start time, and
    the third period being from the second start time to a second completion time, at which hand-over of the workpiece of the second size at the downstream position is completed.

4. The apparatus for manufacturing an absorbent article according to claim 1, further comprising a setting device for setting the upstream position or the downstream position as the hand-over position.

5. The apparatus for manufacturing an absorbent article according to claim 4, wherein:
    the conveying device includes a transfer roll that contacts the holding pad with the continuous sheet and the workpiece therebetween; and
    the setting device positions the transfer roll at one of the upstream position and the downstream position.

6. The apparatus for manufacturing an absorbent article according to claim 1, wherein a deceleration ratio of the circumferential velocity at the second start time relative to the circumferential velocity at the first start time is set to be greater than 1.0.

7. The apparatus for manufacturing an absorbent article according to claim 1, wherein an acceleration ratio of the circumferential velocity at the second start time relative to the circumferential velocity at the first start time is set to be greater than 1.0.

8. A method for manufacturing an absorbent article, the method comprising:
a first conveying step of using a holding pad that rotates along a circling path while velocity of the holding pad is changed to pick up a workpiece at a pick-up position and hand over the workpiece onto a continuous sheet at a hand-over position;
a second conveying step of using a conveying device to convey the continuous sheet at conveying velocity that depends on a size of a product to receive and convey the workpiece on the continuous sheet at the hand-over position;
a step of setting in advance the hand-over position to be one position, depending on the size of the product,
the one position being selected between an upstream position and a downstream position on the circling path, the downstream position being downstream of the upstream position; and
a velocity-changing step in which a velocity-changing device changes circumferential velocity of the holding pad during a period from a first start time to a second start time,
when the size of the product is a first size, hand-over of the workpiece starts at the first start time at the upstream position,
when the size of the product is a second size, hand-over of the workpiece starts at the second start time at the downstream position, and
in the velocity-changing step, the velocity-changing device changing the circumferential velocity of the holding pad so that the circumferential velocity is continuously decelerated or continuously accelerated during the period from the first start time to the second start time,
wherein in the case where the circumferential velocity continuously decelerates, a deceleration ratio of the circumferential velocity at the second start time relative to the circumferential velocity at the first start time is set to be greater than 1.0, and
wherein in the case where the circumferential velocity continuously accelerates, an acceleration ratio of the circumferential velocity at the second start time relative to the circumferential velocity at the first start time is set to be greater than 1.0.

9. The method for manufacturing an absorbent article according to claim 8, wherein the circumferential velocity of the holding pad is changed so that the circumferential velocity is continuously decelerated during the period from the first start time to the second start time in the velocity-changing step.

10. The method for manufacturing an absorbent article according to claim 8, wherein:
for the first size, the conveying velocity is set to the circumferential velocity of the holding pad at the first start time; and
for the second size, the conveying velocity is set to the circumferential velocity of the holding pad at the second start time.

11. The method for manufacturing an absorbent article according to claim 8, wherein the velocity-changing device changes the velocity of the holding pad so that the circumferential velocity is continuously decelerated or continuously accelerated over a first period, a second period, and a third period,
the first period being from the first start time to a first completion time, at which hand-over of the workpiece of the first size is completed,
the second period being from the first completion time to the second start time, and
the third period being from the second start time to a second completion time, at which hand-over of the workpiece of the second size at the downstream position is completed.

12. The method for manufacturing an absorbent article according to claim 8, wherein:
the conveying device includes a transfer roll that contacts the holding pad with the continuous sheet and the workpiece therebetween; and
in the setting step, the transfer roll is positioned at one of the upstream position and the downstream position.

13. The apparatus for manufacturing an absorbent article according to claim 2, further comprising the setting device for setting the upstream position or the downstream position as the hand-over position.

14. The apparatus for manufacturing an absorbent article according to claim 3, further comprising the setting device for setting the upstream position or the downstream position as the hand-over position.

15. The apparatus for manufacturing an absorbent article according to claim 13, wherein:
the conveying device includes a transfer roll that contacts the holding pad with the continuous sheet and the workpiece therebetween; and
the setting device positions the transfer roll at one of the upstream position and the downstream position.

16. The apparatus for manufacturing an absorbent article according to claim 14, wherein:
the conveying device includes a transfer roll that contacts the holding pad with the continuous sheet and the workpiece therebetween; and
the setting device positions the transfer roll at one of the upstream position and the downstream position.

17. The method for manufacturing an absorbent article according to claim 9, wherein:
the conveying device includes a transfer roll that contacts the holding pad with the continuous sheet and the workpiece therebetween; and
in the setting step, the transfer roll is positioned at one of the upstream position and the downstream position.

18. The method for manufacturing an absorbent article according to claim 10, wherein:
the conveying device includes a transfer roll that contacts the holding pad with the continuous sheet and the workpiece therebetween; and
in the setting step, the transfer roll is positioned at one of the upstream position and the downstream position.

19. The method for manufacturing an absorbent article according to claim 11, wherein:
the conveying device includes a transfer roll that contacts the holding pad with the continuous sheet and the workpiece therebetween; and
in the setting step, the transfer roll is positioned at one of the upstream position and the downstream position.

* * * * *